(12) United States Patent
Braido

(10) Patent No.: US 8,915,958 B2
(45) Date of Patent: Dec. 23, 2014

(54) DEVICES FOR TRANSCATHETER PROSTHETIC HEART VALVE IMPLANTATION AND ACCESS CLOSURE

(71) Applicant: St. Jude Medical, Inc., St. Paul, MN (US)

(72) Inventor: Peter Nicholas Braido, Wyoming, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 13/720,176

(22) Filed: Dec. 19, 2012

(65) Prior Publication Data

US 2013/0110228 A1 May 2, 2013

Related U.S. Application Data

(62) Division of application No. 12/451,681, filed on Nov. 24, 2009, now abandoned.

(60) Provisional application No. 60/933,804, filed on Jun. 8, 2007.

(51) Int. Cl.
| | | |
|---|---|---|
| *A61F 2/24* | (2006.01) | |
| *A61B 17/32* | (2006.01) | |
| *A61B 17/00* | (2006.01) | |
| *A61B 17/3205* | (2006.01) | |

(52) U.S. Cl.
CPC ............. *A61F 2/2403* (2013.01); *A61F 2/2436* (2013.01); *A61B 17/32* (2013.01); *A61B 17/0057* (2013.01); *A61B 17/32053* (2013.01); *A61B 2017/320064* (2013.01); *A61B 2017/00575* (2013.01); *A61B 2017/00247* (2013.01); *A61B 2017/00349* (2013.01); *A61B 2017/00592* (2013.01); *A61B 2017/00597* (2013.01); *A61B 2017/00606* (2013.01); *A61B 2017/00867* (2013.01)
USPC .......................................... 623/2.11

(58) Field of Classification Search
CPC ................. A61B 17/0057; A61B 2017/00637; A61B 2017/00575; A61B 2017/00592; A61B 2017/00606; A61B 2017/00641
USPC ...................... 623/2.1, 2.11, 2.12, 2.17, 2.18; 606/213, 215, 216, 232, 233
See application file for complete search history.

(56) References Cited

U.S. PATENT DOCUMENTS

| | | | | |
|---|---|---|---|---|
| 3,874,388 A | * | 4/1975 | King et al. | ..................... 606/232 |
| 4,007,743 A | * | 2/1977 | Blake | ............................ 606/232 |

(Continued)

FOREIGN PATENT DOCUMENTS

| | | |
|---|---|---|
| DE | 10249371 A1 | 4/2003 |
| WO | 2005013836 A1 | 2/2005 |

(Continued)

OTHER PUBLICATIONS

PCT International Search Report date Nov. 27, 2008.

(Continued)

*Primary Examiner* — Jonathan W Miles
(74) *Attorney, Agent, or Firm* — Lerner, David, Littenberg, Krumholz & Mentlik, LLP

(57) ABSTRACT

Apparatus for use in conjunction with implanting a collapsible and re-expandable prosthetic heart valve in a patient by means that are less invasive than traditional open-chest, open-heart surgery. The apparatus may include a one-way valve for preventing blood from escaping from the patient's circulatory system when that system is entered to implant the prosthetic heart valve. The apparatus may include various forms of cutters for gaining access to the patient's circulatory system. The apparatus may include various forms of devices for quickly closing the access to the patient's circulatory system after the prosthetic heart valve has been implanted.

13 Claims, 13 Drawing Sheets

(56) References Cited

U.S. PATENT DOCUMENTS

| | | | |
|---|---|---|---|
| 5,334,217 A * | 8/1994 | Das | 606/213 |
| 5,425,744 A * | 6/1995 | Fagan et al. | 606/213 |
| 5,433,727 A * | 7/1995 | Sideris | 606/213 |
| 5,451,235 A * | 9/1995 | Lock et al. | 606/213 |
| 5,488,958 A | 2/1996 | Topel et al. | |
| 5,505,210 A | 4/1996 | Clement | |
| 5,672,168 A | 9/1997 | de la Torre et al. | |
| 5,702,421 A | 12/1997 | Schneidt | |
| 5,725,552 A * | 3/1998 | Kotula et al. | 606/213 |
| 5,846,261 A * | 12/1998 | Kotula et al. | 606/213 |
| 5,853,422 A | 12/1998 | Huebsch et al. | |
| 5,871,489 A * | 2/1999 | Ovil | 606/148 |
| 6,077,281 A * | 6/2000 | Das | 606/151 |
| 6,077,291 A * | 6/2000 | Das | 606/213 |
| 6,171,329 B1 * | 1/2001 | Shaw et al. | 606/213 |
| 6,180,848 B1 * | 1/2001 | Flament et al. | 623/11.11 |
| 6,214,029 B1 * | 4/2001 | Thill et al. | 606/213 |
| 6,270,500 B1 * | 8/2001 | Lerch | 606/324 |
| 6,270,515 B1 * | 8/2001 | Linden et al. | 606/213 |
| 6,312,446 B1 * | 11/2001 | Huebsch et al. | 606/213 |
| 6,656,206 B2 * | 12/2003 | Corcoran et al. | 606/213 |
| 6,755,867 B2 * | 6/2004 | Rousseau | 623/23.64 |
| 6,913,614 B2 * | 7/2005 | Marino et al. | 606/213 |
| 7,087,072 B2 * | 8/2006 | Marino et al. | 606/213 |
| 7,318,833 B2 * | 1/2008 | Chanduszko | 606/215 |
| 7,431,729 B2 * | 10/2008 | Chanduszko | 606/213 |
| 7,479,155 B2 * | 1/2009 | Gainor et al. | 606/213 |
| 2003/0055455 A1 | 3/2003 | Yang et al. | |
| 2003/0225402 A1 | 12/2003 | Stevens et al. | |
| 2004/0044364 A1 * | 3/2004 | DeVries et al. | 606/213 |
| 2004/0049221 A1 | 3/2004 | Loshakove et al. | |
| 2004/0073242 A1 * | 4/2004 | Chanduszko | 606/157 |
| 2004/0143277 A1 * | 7/2004 | Marino et al. | 606/157 |
| 2004/0143291 A1 * | 7/2004 | Corcoran et al. | 606/213 |
| 2004/0143292 A1 * | 7/2004 | Marino et al. | 606/213 |
| 2004/0143293 A1 * | 7/2004 | Marino et al. | 606/213 |
| 2004/0143294 A1 * | 7/2004 | Corcoran et al. | 606/213 |
| 2004/0176799 A1 | 9/2004 | Chanduszko et al. | |
| 2004/0225324 A1 * | 11/2004 | Marino et al. | 606/213 |
| 2005/0065548 A1 * | 3/2005 | Marino et al. | 606/213 |
| 2005/0277982 A1 * | 12/2005 | Marino et al. | 606/213 |
| 2006/0241690 A1 * | 10/2006 | Amplatz et al. | 606/213 |
| 2006/0247680 A1 * | 11/2006 | Amplatz et al. | 606/213 |

FOREIGN PATENT DOCUMENTS

| | | |
|---|---|---|
| WO | 2005094525 A2 | 10/2005 |
| WO | 2008036384 A2 | 3/2008 |

OTHER PUBLICATIONS

Tozzi et al, "Endoscopic Off-Pump Aortic Valve Replacement: Does the Pericardial Cuff Improve the Sutureless Closure of Left Ventricular Access?", European Journal of Cardiaothorac Surg. Jan. 2007; 31(1):22-5, Epub Sep. 6, 2006.

European Search Report for Application No. EP12192074 dated Aug. 5, 2013.

* cited by examiner

DEVICES FOR TRANSCATHETER PROSTHETIC HEART VALVE IMPLANTATION AND ACCESS CLOSURE

CROSS-REFERENCE TO RELATED APPLICATIONS

This application is a divisional application of U.S. application Ser. No. 12/451,681, filed on Nov. 24, 2009, which claims the benefit of the filing date of U.S. Provisional Patent Application No. 60/933,804, filed Jun. 8, 2007, the disclosures of which are hereby incorporated herein by reference in their entireties.

BACKGROUND OF THE INVENTION

Thousands of high-risk patients with severe aortic stenosis go untreated each year because they are deemed inoperable for conventional, open-chest/open-heart surgical heart valve replacement. In an attempt to treat these patients, collapsible prosthetic heart valves have been developed to be inserted within the stenotic leaflets of these patients via transapical (i.e., through the apex of the heart) or other means that are less invasive than full open-chest, open-heart surgery. (See, for example, P. Tozzi et al., "Endoscopic off-pump aortic valve replacement: does the pericardial cuff improve the sutureless closure of left ventricular access?", European Journal of Cardiothoracic Surgery 31 (2007) 22-25, available online 6 Sep. 2006.) For convenience herein, all such approaches that involve passing a collapsed prosthetic heart valve through a relatively small tubular instrument in order to get the valve into the patient to the desired implant site (where the valve is re-expanded to its operable size) may be referred to as transcatheter approaches. It will be appreciated that the tubular valve-delivery instrument employed can be catheter-like, trocar-like, endoscope-like, laparoscopic or of any other generally similar construction.

Currently a purse string suture is tightened to close off the apex of the heart (or other tissue structure being used for access) after that tissue has been punctured. However, existing methods and devices may not sufficiently address several issues, such as: (1) blood loss and optimal field of view, (2) friable tissue, (3) time and quality of sealing, (4) air embolization, etc. The designs of this invention are transcatheter designs that deliver high-risk patients with a prosthetic heart valve and subsequently seal the apex or other access without many of the associated possible difficulties.

SUMMARY OF THE INVENTION

Disclosed herein are apparatus for closing an aperture through a wall of a structure within a patient's circulatory system. The apparatus may include a central structure having a longitudinal axis, a first portion operatively coupled to the central structure, and second portion operatively coupled to the central structure. The first portion may be transitionable between a collapsed condition and an expanded condition, and may extend radially outward from the longitudinal axis by a greater amount in the expanded condition than in the collapsed condition. The first portion may be configured to conform to an inner surface of tissue around the aperture when in the expanded condition. The second portion may be transitionable between a collapsed condition and an expanded condition and may extend radially outward from the longitudinal axis by a greater amount in the expanded condition than in the collapsed condition. The second portion may be configured to conform to an outer surface of tissue around the aperture when in the expanded condition. The apparatus may have a longer length when the first portion and the second portion are in the collapsed condition than when the first portion and the second portion are in the expanded condition. The first portion and the second portion may be resiliently biased toward the expanded condition. The central structure may be configured to substantially fill the aperture. The central structure also may be configured to hold the first portion against the inner surface of tissue around the aperture and to hold the second portion against the outer surface of tissue around the aperture.

The first portion may have a convex shape in the expanded condition as viewed from the second portion. The second portion may have a concave shape in the expanded condition as viewed from the first portion. The first portion may have a cup-like shape, an arcuate shape, or the shape of an arcuate surface of a cylinder in the expanded condition. The first portion may include a plurality of members projecting radially outward from the longitudinal axis in the expanded condition, or a plurality of members that spiral out from the longitudinal axis in the expanded condition, or a web that projects radially out from the longitudinal axis in the expanded condition. Alternatively, the first portion may include a plurality of members that extend radially outward from the longitudinal axis in the expanded condition, each of the members having a U-shaped configuration with an open end and a closed end, the closed end being radially outermost from the longitudinal axis. Still further, the first portion may include a plurality of members that intersect one another in a mesh pattern and that extend radially outward from the longitudinal axis in the expanded condition.

These and other embodiments of the present disclosure are more fully described hereinbelow.

DETAILED DESCRIPTION

The following discussion will (at least initially) make frequent references to access through the apex of the heart (e.g., through the apex of the left ventricle). It will be understood, however, that the invention is equally applicable to access via other routes (e.g., through the apex of the right ventricle, through a major vessel such as the aorta or the vena cava, through either of the atria, through the left atrial appendage, etc.). Thus the prosthetic heart valve may be delivered from the outflow side (e.g., the aorta) or the inflow side (e.g., the apex). Similarly, the access closure devices of this invention can be shaped to close an access through the side wall of a vessel like the aorta (access closure device shaped like arcuate parts of the walls of concentric cylindrical tubes (e.g., FIG. 10)), or they can be shaped to close an apical access (access closure device shaped like nesting cups or cones (e.g., FIGS. 4 and 9)). Also, although left ventricular ("LV") access for aortic valve replacement may be mentioned most frequently in the following, the invention is also applicable to LV access for mitral valve replacement and to right ventricular ("RV") access for pulmonic valve replacement, etc.

The designs of this invention may be for use within patients who may need an aortic or other valve replacement, but are not otherwise treated adequately. The designs of this invention utilize a transcatheter, collapsible and subsequently re-expandable, prosthetic heart valve delivery and implant system and an apical or other access closure device (see the accompanying drawings and the following further description).

Figure 1:
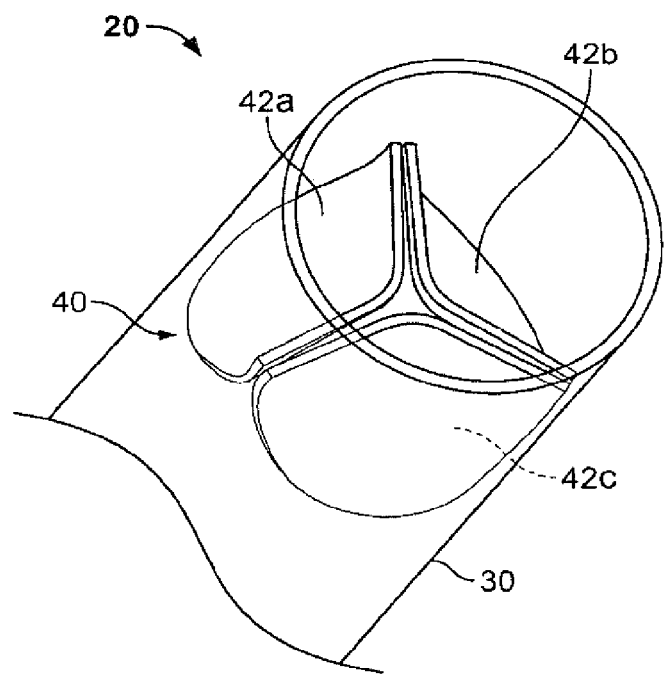
FIG. 1 is a simplified isometric or perspective view of an illustrative embodiment of possible apparatus in accordance with the invention.

A coring device 10 (e.g., FIGS. 2A, 2B, 3A, 3B), a collapsible and re-expandable prosthetic heart valve (not shown), and a closure device (e.g., as shown in any of FIG. 4-10) can be used with or without passing through a temporary sealing apparatus 20 (e.g., as shown in FIG. 1). A sealing apparatus can include a one-way polymer valve located distal to the apex or other access (FIG. 1). This can allow for the cutting (coring) device to be retracted through this valve, while still maintaining a sealed environment.

To amplify what is shown in FIG. 1, this FIG. shows the distal end portion of an elongated delivery sheath 30 that, in use, is passed through an aperture that is created in a patient's circulatory system tissue in the vicinity of the patient's native heart valve that is to be replaced by a collapsible and re-expandable prosthetic heart valve. This distal end portion of delivery sheath 30 may be introduced into the patient using techniques that are less invasive than traditional full open-chest open-heart surgery. A proximal portion of delivery sheath 30 may remain outside the patient's body at all times so that the user of the apparatus can at least to some extent control the distal portion by manipulating the accessible (external to the patient) proximal portion. Various types of instrumentation (including the prosthetic heart valve in its collapsed condition) may be introduced into the patient via the lumen that extends longitudinally through delivery sheath 30. Sheath 30 may be made with any desired degree of lateral flexibility or stiffness, depending, for example, on how it is intended that the apparatus will be used to enter the patient and approach the heart valve to be replaced.

As shown in FIG. 1, the distal portion of delivery sheath 30 includes a valve 40 that acts as a one-way check valve for substantially preventing fluid (primarily blood) from flowing through the lumen of sheath 30 from the upper right as viewed in FIG. 1 to the lower left as viewed in that FIG. Valve 40 is preferably made of flexible polymer material. For example, valve 40 may include three approximately half-moon shaped leaflets 42a-c. The curved edge of each leaflet 42 (toward the lower left in FIG. 1) is secured in a fluid-tight (or sealing) manner to the inner surface of sheath 30. The straighter edge of each leaflet (toward the upper right in FIG. 1) is the "free" edge of the leaflet. The leaflets are sized, shaped, and mounted in sheath 30 so that there is sufficient slack in the free edges to enable those free edges to come together in a Y-like pattern (as shown in FIG. 1) to close the valve (i.e., in response to fluid pressure on the leaflets from the upper right). However, objects such as other instrumentation can be pushed through the valve from the lower left (and also subsequently pulled back through the valve). The valve leaflets are preferably sufficiently flexible so that they provide a good fluid seal around any instrumentation pushed through them. Of course, the leaflets also resiliently re-close after such instrumentation is pulled back through them.

The coring devices 10 shown in FIGS. 2A-3B are examples of instrumentation that can be introduced into the patient via the lumen in delivery sheath 30. For example, delivery sheath 30 can be advanced into the patient until its distal end is against the patient's circulatory system tissue that is to be cut to gain access to the interior of that system. Then coring device 10 can be extended from the distal end of sheath 30 to cut an aperture through the tissue. Delivery sheath 30 may then be pushed through the tissue aperture (formed by coring device 10) into the circulatory system closer to the native heart valve that is to be replaced. Coring device 10 can then be withdrawn from sheath 30 (which can include pulling the coring device back (i.e., proximally) through valve 40). Other instrumentation (ultimately including the prosthetic heart valve) can thereafter be introduced into the patient through the lumen of delivery sheath 30. Again, this can include passing this other instrumentation through valve 40. When the heart valve replacement procedure is complete, an access closure device in accordance with this invention (e.g., as shown in any of FIGS. 4A-10, and as described later in this specification) can be introduced into the patient via the lumen of sheath 30 and deployed to close the aperture in the patient's circulatory system as sheath 30 is withdrawn from that aperture and ultimately from the patient.

We turn now to more details regarding possible coring devices, e.g., as shown in FIGS. 2A-3B.

Although the apex of the heart or other access could be punctured by traditional means, coring devices (e.g., as shown in FIGS. 2A-3B) can be integrated into the delivery system and can have any of several configurations.

Figure 2A:
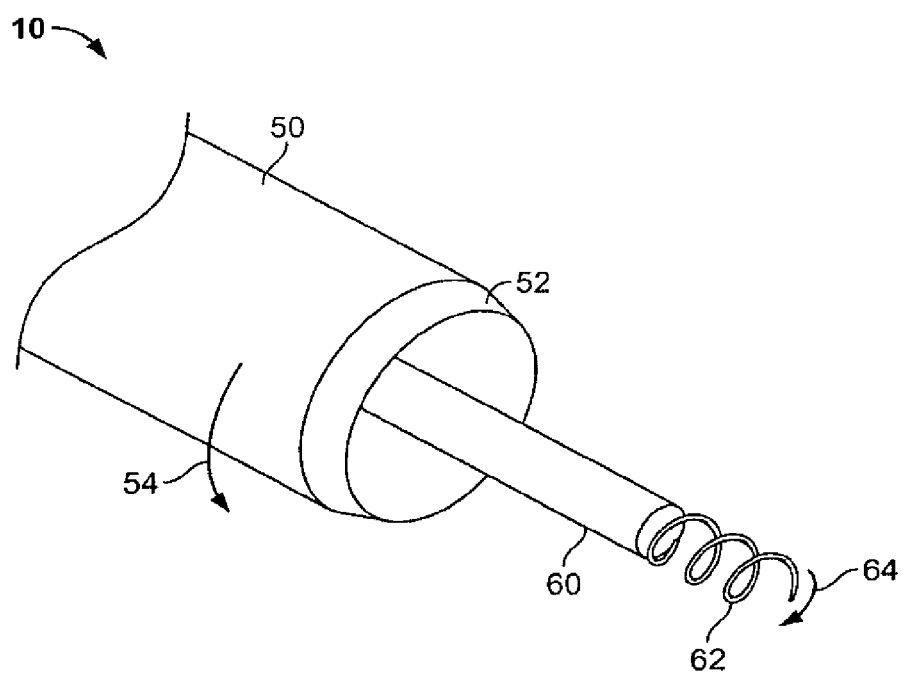
FIG. 2A is a simplified isometric or perspective view of an illustrative embodiment of other possible apparatus in accordance with the invention.
Figure 2B:
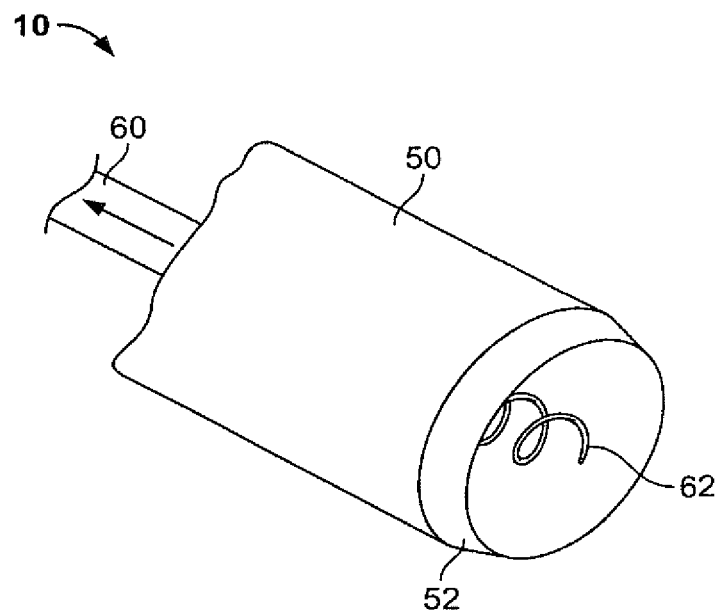
FIG. 2B is similar to FIG. 2A, but shows the FIG. 2A apparatus in another operating condition in accordance with the invention.

As shown in FIGS. 2A and 2B, a first illustrative embodiment of a coring device 10 includes an elongated tube 50, only a distal portion of which is visible in these FIGS. The extreme distal end of tube 50 is provided with a sharp edge portion 52. Edge 52 is sharp enough to cut through tissue of the patient's circulatory system. Tube 50 may be rotated about its central longitudinal axis (e.g., as indicated by arrow 54) to help edge 52 cut through tissue. Edge 52 makes a circular aperture through the tissue that it cuts. As mentioned earlier, coring device 10 (including tube 50) is suitable for delivery into the patient via the lumen of delivery sheath 30. A proximal portion (not shown) of coring device 10 typically remains outside the patient at all times so that the operator of the apparatus can access it and use such access to control operation of the distal portion.

Additional structure of coring device 10 is tissue engaging, stabilizing, and capture structure 60. (Again only the distal portion of structure 60 is visible in FIGS. 2A and 2B.) Elongated structure 60 (principally a shaft) is disposed substantially concentrically and coaxially inside tube 50, and is axially reciprocable relative to tube 50 along the length of those elements (50 and 60). FIG. 2A shows structure 60 extended distally relative to tube 50, while FIG. 2B shows structure 60 retracted proximally relative to tube 50. Structure 60 is also rotatable about its longitudinal axis relative to tube 50.

The distal end of structure 60 includes a corkscrew-like member 62. Corkscrew 62 has a sharp distal tip which can easily penetrate tissue of the patient's circulatory system. When corkscrew 62 is adjacent to tissue of the patient's circulatory system, shaft 60 can be used to rotate the corkscrew in the direction indicated by arrow 64, and to (at the same time) push the corkscrew in the distal direction. These operations cause corkscrew 62 to penetrate and thread itself into the patient's tissue like a corkscrew going into a cork. When the patient's tissue is sufficiently securely engaged by corkscrew 62 in this manner, threading of the corkscrew into the tissue can be stopped. With the patient's tissue thus now engaged, held, and stabilized by the corkscrew, sharped edge 52 can be pushed into the tissue around corkscrew 62 and at the same time rotated as indicated by arrow 54 to cut a circular aperture through the tissue around the corkscrew. Rotation of edge 52 in the opposite direction from the earlier rotation of corkscrew 62 is preferred for not dislodging the disc of tissue cut away by edge 52 from secure retention by corkscrew 62. In other words, corkscrew 62 helps to hold the tissue so that it is stable for cutting by edge 52. In addition, after edge 52 has completely cut through the tissue, corkscrew 62 holds the disc of tissue that edge 52 has cut around and away from the patient's other tissue so that this tissue disc cannot escape from the apparatus. FIG. 2B shows a typical condition of the apparatus after edge 52 has been advanced (distally) sufficiently far to cut through the patient's tissue. The disc of tissue thus cut out by edge 52 will be inside tube 50 around and securely retained by corkscrew 62.

Figure 3A:
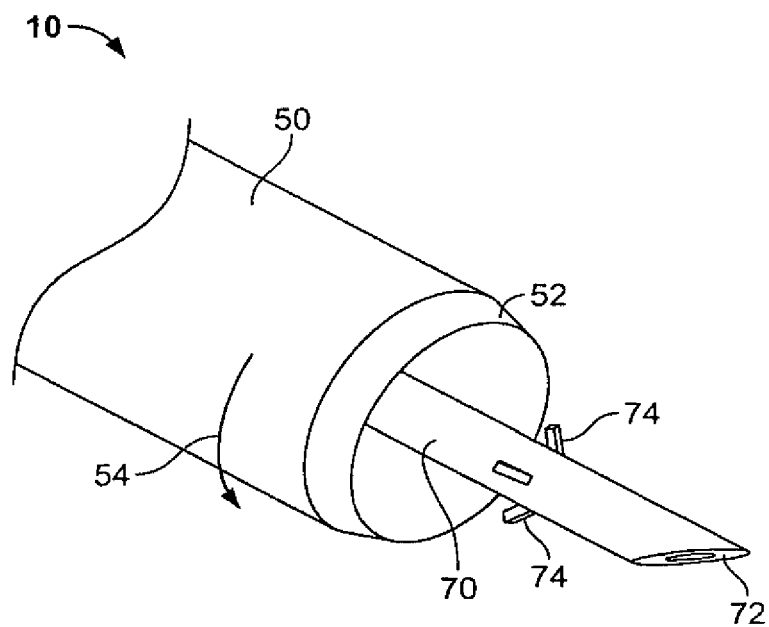
FIG. 3A is a simplified isometric or perspective view of an illustrative embodiment of still other possible apparatus in accordance with the invention.
Figure 3B:
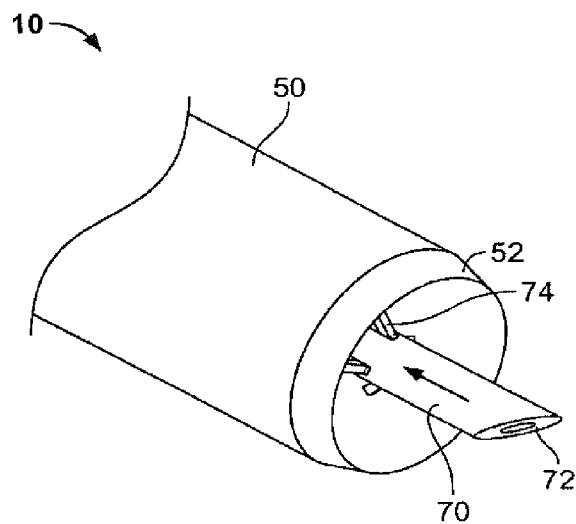
FIG. 3B is similar to FIG. 3A, but shows the FIG. 3A apparatus in another operating condition in accordance with the invention.

In the alternative embodiment shown in FIGS. 3A and 3B elements 50, 52, and 54 can be the same as the correspondingly numbered elements in FIGS. 2A and 2B. These elements therefore do not need to be described again. The main difference between this embodiment and the embodiment of FIGS. 2A and 2B is in the tissue engaging, stabilizing, and retaining structure inside tube 50. In the FIGS. 3A and 3B embodiment this may include a length of hypotube or hypotube-like material 70 with a sharply pointed, tissue penetrating, distal tip 72, and with tissue retaining barbs 74 just proximal of distal tip 72. Unlike structure 60, which must be rotated to thread corkscrew 62 into tissue, the distal end 72 of tube 70 is small enough and sharp enough to be pushed straight into and through the patient's circulatory system tissue. Barbs 74 extend radially outwardly from tube 70, but are also inclined back in the proximal direction as they extend radially outwardly. Accordingly, barbs 74 can enter the tissue relatively easily as tube 70 moves in the distal direction into the tissue (e.g., as in FIG. 3A). But (because of their "backward" incline) barbs 74 strongly resist being pulled proximally out of the tissue after they have entered or passed through the tissue. Accordingly, after structure 70/72/74 has entered the patient's tissue, that structure acts to hold and stabilize the tissue while edge 52 is pushed distally and rotated to cut a circle through the tissue around structure 70/72/74 (e.g., as shown in FIG. 3B). After edge 52 has thus cut through the tissue, structure 70/72/74 acts to retain the disc of tissue that has thus been cut free and to keep that tissue disc from escaping from the apparatus.

Except for the differences thus described above, the embodiment shown in FIGS. 3A and 3B can be constructed and operated (employed) similar to the embodiment shown in FIGS. 2A and 2B. The following recapitulates and in some respects extends what is said above about these various embodiments.

The corkscrew coring mechanism (FIGS. 2A and 2B) includes the following features:

1) A circular cutting device 50 with a handle on the proximal end (not shown) and a tapered sharp edge 52 on the distal end. The cutter can be made of several biocompatible metal materials, such as stainless steel 316.

2) A corkscrew configuration 62 on the end of a rod 60 is inserted into the tissue and rotated until the tissue abuts the flat section of the rod (at the proximal end of corkscrew 62). The cutter 50 is rotated in the opposite direction of the corkscrew 62 to ensure that the tissue does not escape.

3) During the rotation procedures, the corkscrew rod 60 is translated toward the proximal end of the device to allow the cutter 50 to dissect and remove the tissue.

The spire coring mechanism (FIGS. 3A and 3B) includes the following features:

1) A circular cutting device 50 with a handle on the proximal end (not shown) and a tapered sharp edge 52 on the distal end.

2) A large needle-like protrusion 70/72 with spires 74 possibly laser cut from the tube. The spires (barbs) can be fixed at a specified angle and annealed into place. The small tube 70 is sharp on one end 72 to pierce the tissue, and is only hollow on the distal portion.

3) The cutter 50 is rotated as the spire device translates proximally to draw in the tissue.

After the prosthetic heart valve (not shown) has been deployed in the patient as a replacement for the patient's native heart valve, quick and secure attachment of a closure device to the apex of the heart (or other access aperture) previously cut into the patient's circulatory system without the use of sutures as the primary attachment method can take any of several forms. In general, all of these closure devices contract and expand in some manner to hold onto the aforementioned tissue. For example, these closure devices may contract for delivery into the patient through delivery sheath 30 or similar tube-like instrumentation, and they may then expand to engage the patient's tissue around the access aperture and to close that aperture. (Sutures may be used for supplemental securement of the closure device to the patient's tissue.) Several illustrative embodiments of such closure devices are shown in FIGS. 4A-10 and are described in the following.

Some of the closure devices shown herein and described below can be cut from a tube or braided with wire made from a shape-memory alloy (e.g., nitinol) so that they are self-expanding. The closure device designs of this invention can have several features that other known designs do not have.

Figure 4A:
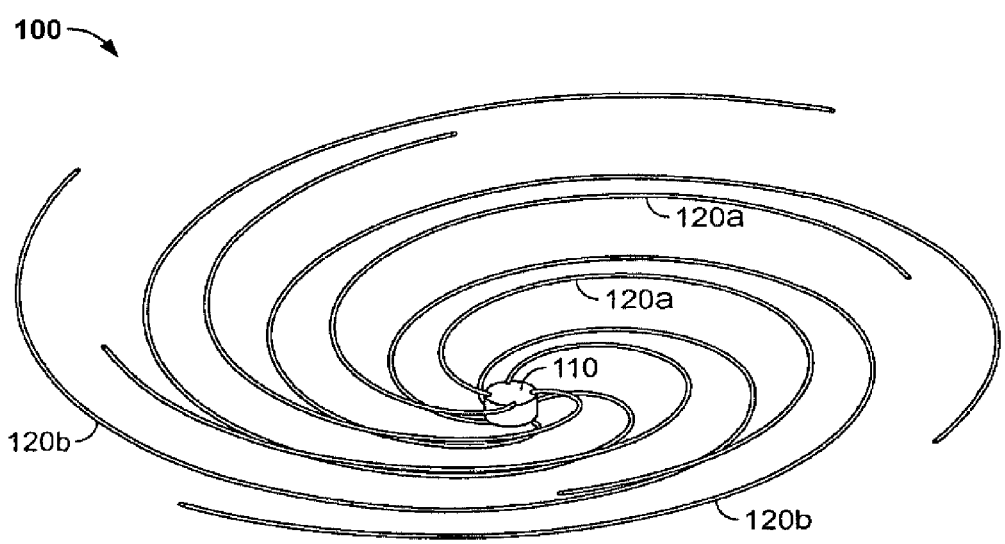
FIG. 4A is a simplified isometric or perspective view of an illustrative embodiment of other possible apparatus in accordance with the invention.
Figure 4B:
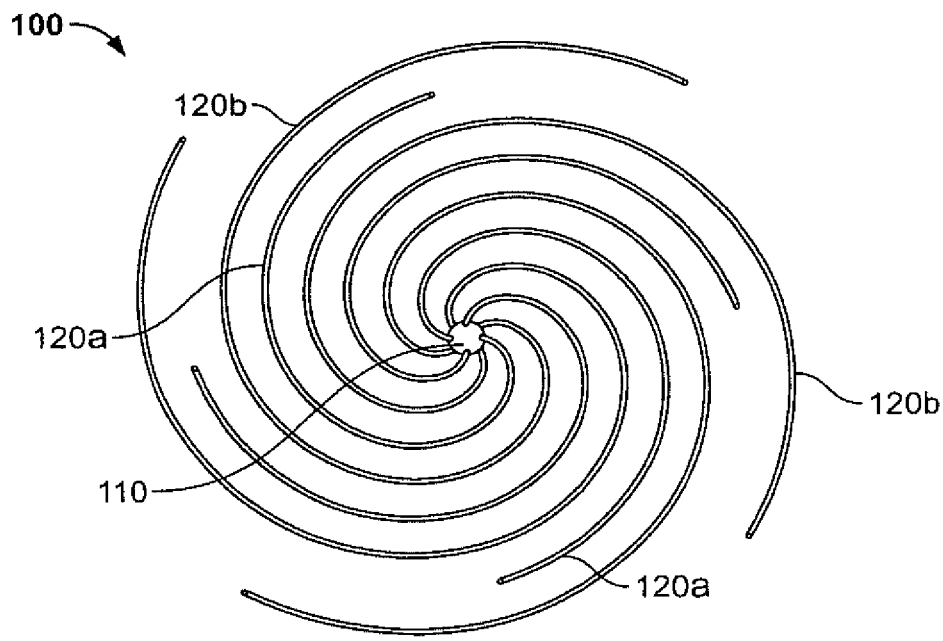
FIG. 4B is a simplified view, from another angle, of what is shown in FIG. 4A.
Figure 4C:
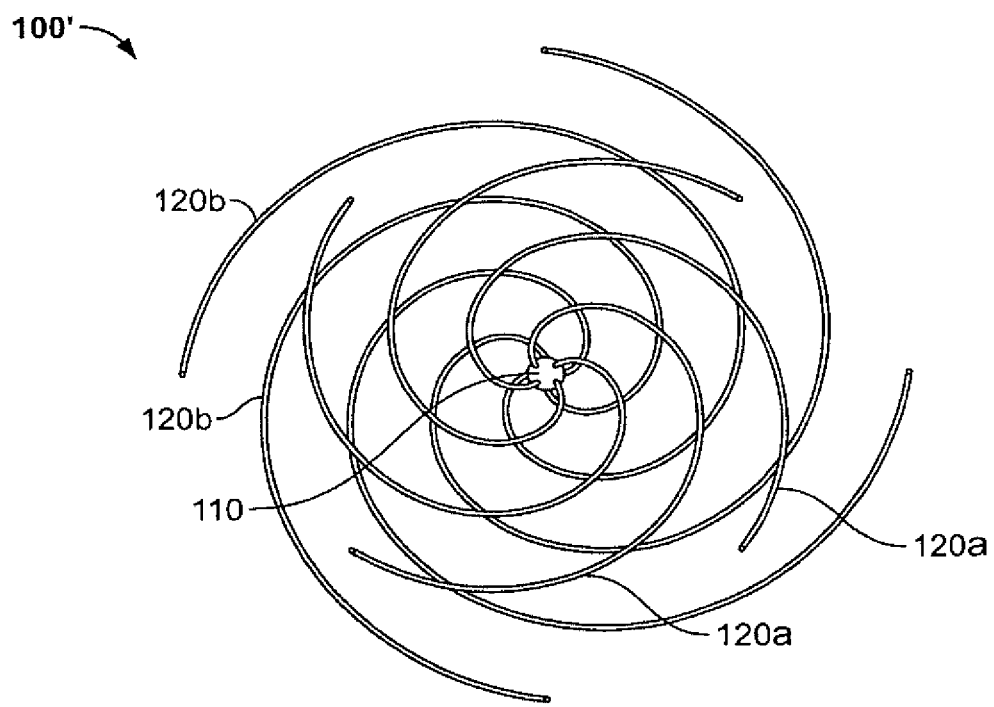
FIG. 4C is similar to FIG. 4B for an alternative embodiment of what is shown in FIGS. 4A and 4B in accordance with the invention.
Figure 4D:
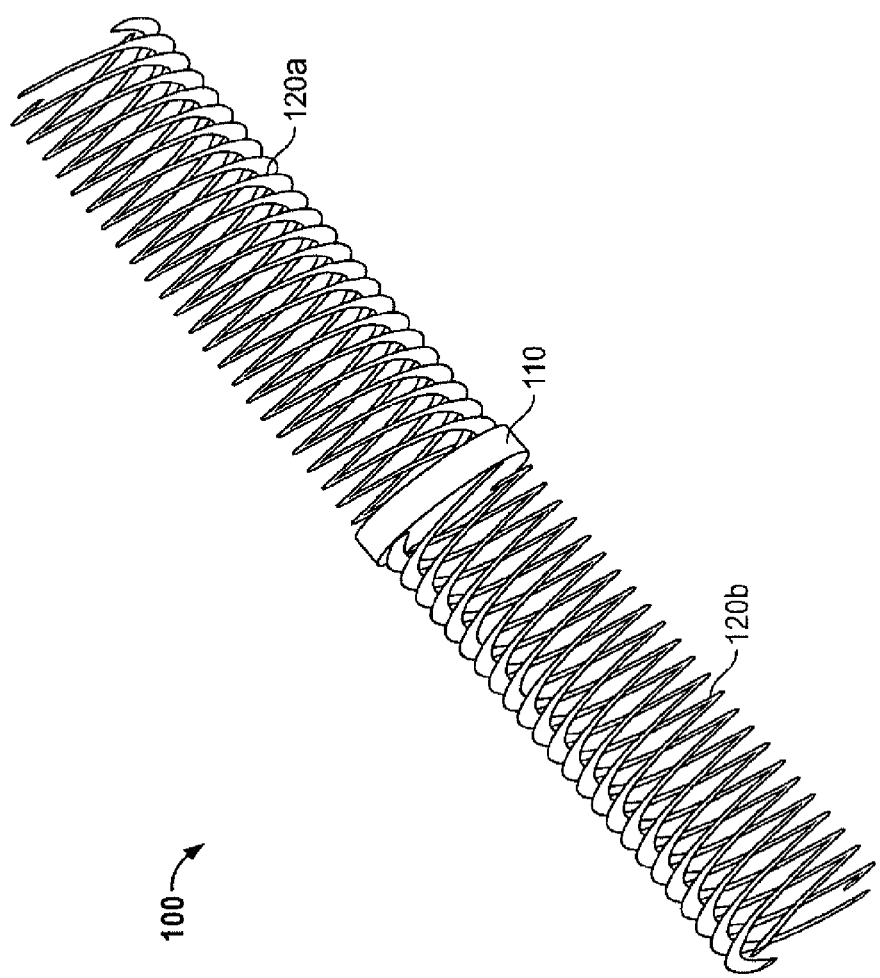
FIG. 4D is a simplified isometric or perspective view of apparatus like that shown in FIGS. 4A-4C in another operating condition in accordance with the invention.

A first illustrative embodiment of a closure device 100 in accordance with the invention is shown, at least in part, in FIGS. 4A-4D. FIG. 4D shows closure device 100 in its collapsed condition (e.g., the condition in which it can be delivered (substantially coaxially) into the patient lumen of delivery sheath 30 or the like). FIGS. 4A-4C show several views of closure device 100 in its expanded (spiral) condition. In fact, FIG. 4C shows a slight modification relative to the other FIGS. in this group. In this modification (which is given reference number 100') the two sets of fingers spiral out from the center in opposite directions. In all other respects the FIG. 4C structure can be the same as the other FIG. 4 structures, and so all of the FIG. 4 structures will sometimes be referred to generically as structure 100 or as closure device 100.

Closure device 100 includes a central member 110, which as the origin of and anchor for two sets of fingers 120a and 120b that are resiliently biased to spiral out from the central member as shown in any of FIGS. 4A-4C. Central member 110 also acts as a spacer between these two sets of fingers 120a and 120b. Thus in FIG. 4A, for example, fingers 120a may be referred to as the upper set of fingers or spirals, and fingers 120b may be referred to as the lower set of fingers or spirals. In use in a patient, central member 110 typically resides in the access aperture that has been cut through tissue of the patient's circulatory system (and which aperture it is now desired to close), with one set of fingers 120a spiraling out from central member 110 against the inner surface of the circulatory system tissue that surrounds the access aperture, and with the other set of fingers 120b spiraling out from central member 110 against the outer surface of the circulatory system tissue that surrounds the access aperture. The spacing (along the length of central member 110) between the two sets of fingers is preferably similar to or slightly less than the thickness of the tissue around the access aperture.

In addition to spiraling radially out, fingers 120a and 120b may be resiliently biased to deploy into an overall geometric shape that conforms to the shape of the tissue surfaces that these sets of fingers are intended to engage (lie against as described in the preceding paragraph). Suppose, for example, that device 100 is intended for use in closing an access aperture through the apex of the heart. Then fingers 120a may be resiliently biased to spiral out into a cup-like geometric shape (similar to the shape of the inner surface of the heart muscle wall near the apex of the heart). Similarly, fingers 120b may be resiliently biased to spiral out into another cup-like geometric shape (having a nesting relationship with the first-mentioned cup shape, and which is similar to the shape of the outer surface of the heart muscle wall near the apex of the heart). The shape, extent, and spacing between the sets of fingers 120a and 120b are preferably such as to enable closure device 100 to securely engage the tissue surrounding the access aperture from both sides (inside and outside) of the tissue in order to securely anchor the closure device to the patient's tissue, again with central member 110 actually in and passing through the access aperture.

Central member 110 may itself be large enough and sufficiently impervious to blood flow to occlude the access aperture and thereby provide the desired closure of that aperture. Alternatively, one or both sets of spiral fingers 120a/120b (and/or even central member 110) may support a web or sheet of blood-impervious material (not shown) over all or appropriate parts of that structure to provide complete closure of the access aperture. Examples of suitable materials and constructions for such a sheet of blood-impervious material include (1) a fiber-supported silicone, (2) a silicone sheet within a polyester fabric (like the sewing cuff on certain prosthetic heart valves), (3) collagen-impregnated polyester {as in certain synthetic blood vessel grafts), etc.

Recapitulating and in some respects extending the foregoing, the spiral closure mechanism (FIG. 4) can have the following features:

1) Spirals 120 collapse when in a delivery system (e.g. 30) and expand to conform to anatomy when deployed.

2) The movable members 120 can be made from a shape-memory alloy wire, tube, or flat sheet.

3) The device may also include (a) fabric web or sheet (not shown) sutured or sonically welded, or (b) sutured tissue (also not shown), between movable members 120 in one or both sets of such members to ensure proper sealing and tissue in-growth. Examples of suitable tissue types for this and other generally similar uses throughout this disclosure include peritineum, sub-mucosa, and pericardial tissue.

4) Members 120 can form two concentric, mating, or nesting cups or cones to attach to the internal and external aspects of the apex of the heart (see, e.g., FIG. 4A).

5) Spirals 120 can rotate in the same direction (FIGS. 4A and 4B) to conform to the heart during its spiral-like contractions during systole, or can be in opposite directions (FIG. 4C).

6) The device can be deployed with both sides attached to a center hinge section 110, or can be ratcheted, screwed, etc., together separately. In other words, each set of fingers 120 and some associated central structure 110 can be initially separate, and these two initially separate structures can be secured together (via their central parts) to provide a complete closure device 100.

7) Center hinge point 110 can be rigid, semi-rigid, or made of a flaccid fabric to allow closure of the hole and optimal sealing.

Figure 10:
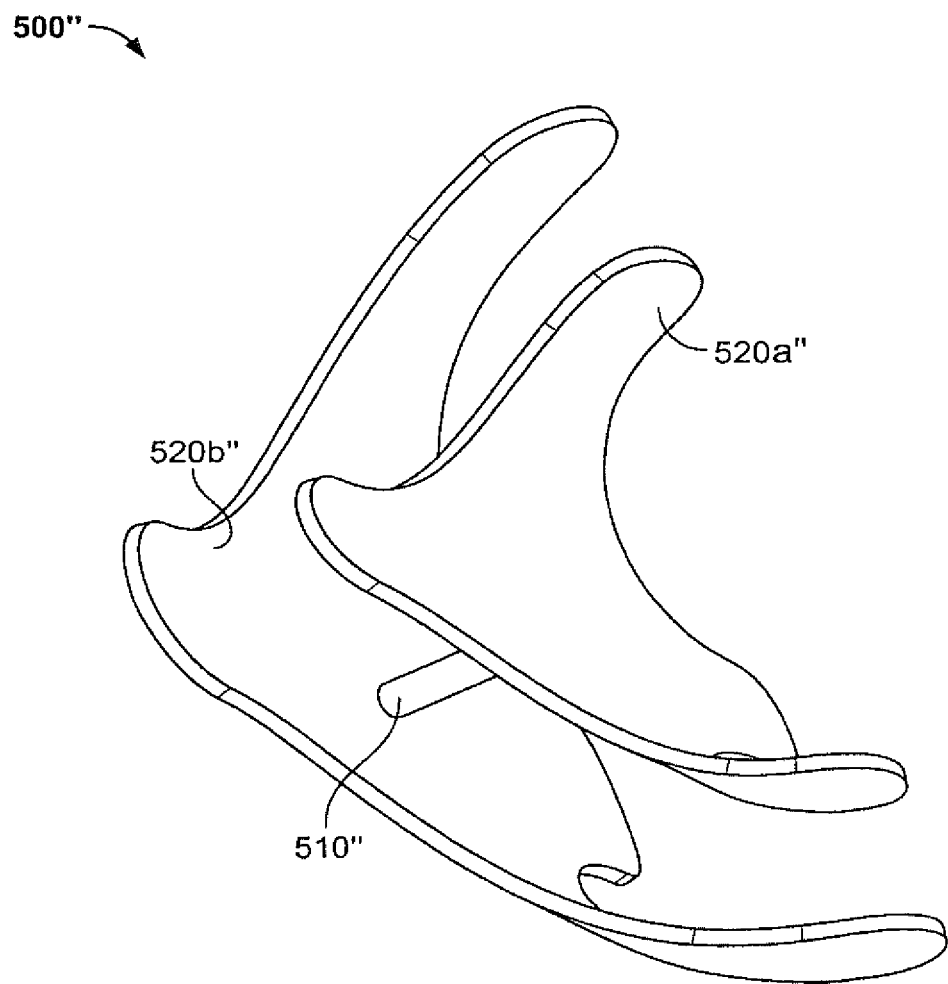
FIG. 10 is a simplified isometric or perspective view of another possible form of apparatus of the type shown in FIG. 9 in accordance with the invention.

An example of how this and other closure devices of this invention may "conform to anatomy when deployed" (e.g., points 1 and 4 immediately above) has already been provided, but can be more fully explained as follows. The incision or opening to be closed may be through the wall of the heart at or near the apex of the heart. At such a location the wall of the heart is cup- or cone-shaped (concave as viewed from inside the heart; convex as viewed from outside the heart). To conform to the anatomy at such a location, each of the two spaced spiral structures 120 in FIG. 4 (e.g., the upper spiral structure 120a as viewed in FIG. 4A, which is deployed inside the heart, and the lower spiral structure 120b as viewed in FIG. 4A, which is deployed outside the heart) is similarly cup- or cone-shaped when deployed (i.e., concave as viewed from above in FIG. 4A, and convex as viewed from below in FIG. 4A). Alternatively, if the incision or opening to be closed is through a tissue structure having a different shape than the apex of the heart, then the closure device may have another deployed shaped to conform to that anatomy. For example, FIG. 10 shows a deployed closure shape that may be suitable for closing an opening in the side wall of a tubular vessel such as the aorta. Thus, in FIG. 10 the two main members of the closure device are shaped like arcuate portions of the walls of two concentric cylindrical tubes. The element with the smaller radius of curvature would be deployed inside the tubular vessel to be closed, and the larger curvature element would be deployed outside the vessel to be closed.

Figure 5A:
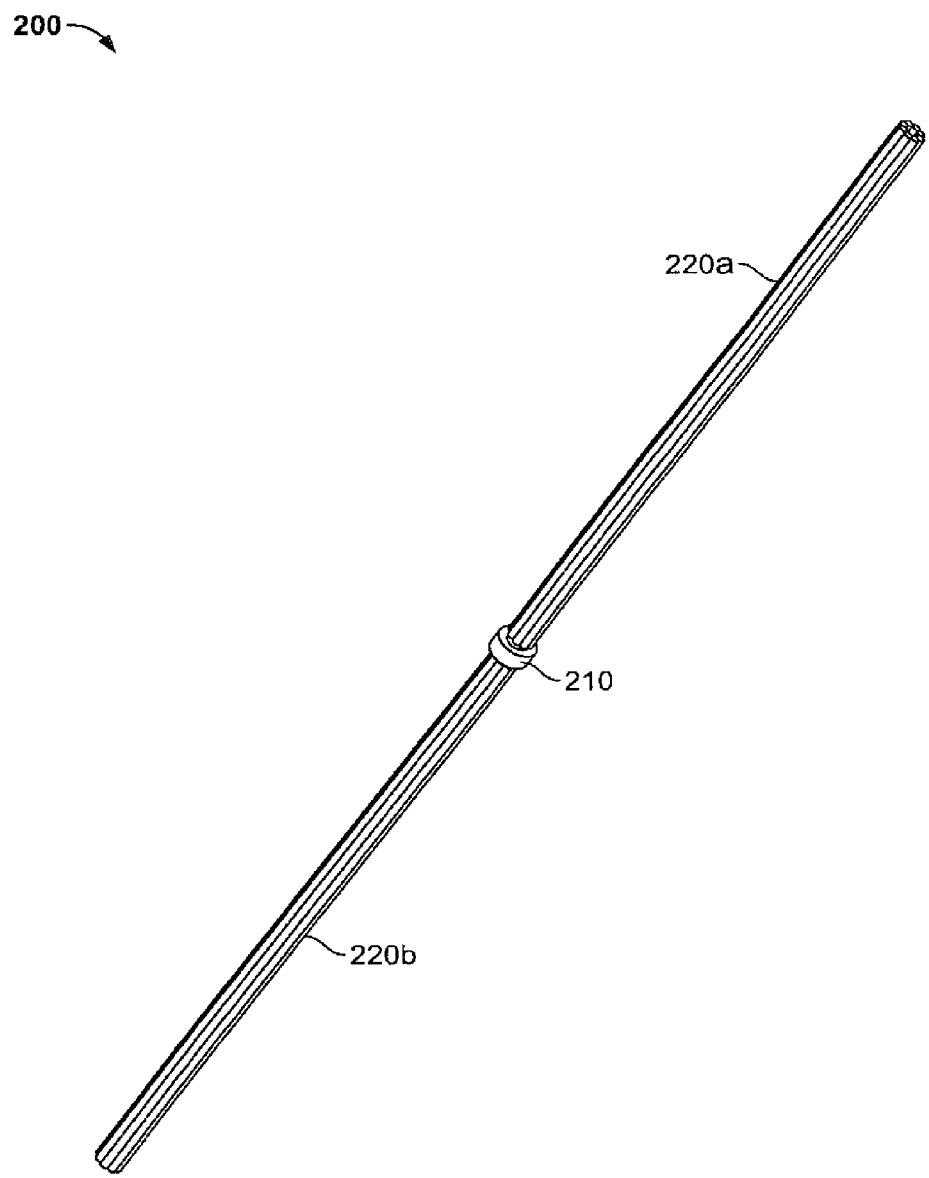
FIG. 5A is a simplified isometric or perspective view of an illustrative embodiment of still other possible apparatus in accordance with the invention.
Figure 5B:
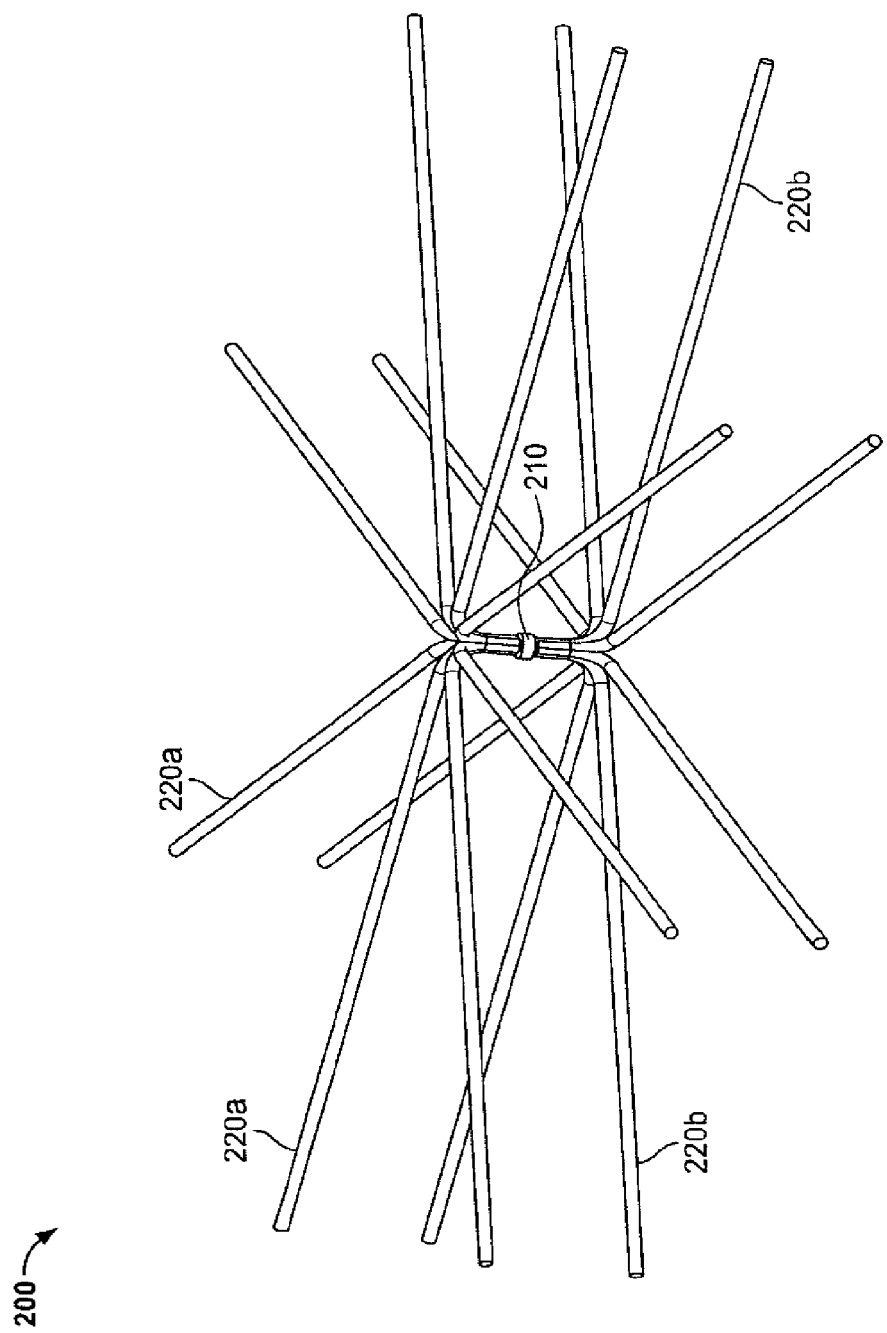
FIG. 5B is a simplified isometric or perspective view of the FIG. 5A apparatus in another operating condition in accordance with the invention.

An alternative embodiment of a tissue access aperture closure device 200 in accordance with the invention is shown in FIGS. 5A and 5B. This type of structure may sometimes be referred to as a spider design. FIG. 5A shows closure device 200 in its collapsed condition (e.g., the condition in which it can be delivered into the patient via the lumen through delivery sheath 30 or the like). FIG. 5 B shows closure device 200 in its expanded condition (i.e., the condition in which it is deployed in the patient to close the access aperture through the patient's circulatory system tissue).

Closure device 200 includes a central structure 210. Attached to each end of structure 210 is a respective set of fingers 220a or 220b that is resiliently biased to project radially out from structure 210 like the spokes of a wheel. As viewed in FIG. 5 A, fingers 220a can be elastically deflected upwardly until they are substantially parallel to one another for the collapsed condition shown in FIG. 5A. Similarly, fingers 220b can be elastically deflected downwardly until they are substantially parallel to one another for the FIG. 5A collapsed condition. When fingers 220 are released from constraint (e.g., as a result of device 200 being pushed from the distal end of a hollow, tubular delivery apparatus), the fingers elastically (resiliently) return to the condition shown in FIG. 5B (i.e., the deployed condition of closure device 200).

As in the case of closure device 100, closure device 200 is typically deployed in the patient with central structure 210 passing through the tissue aperture to be closed, with fingers 220a extending radially out from structure 210 against the inner surface of the tissue that surrounds the aperture, and with fingers 220b extending radially out from structure 210 against the outer surface of the tissue that surrounds the aperture. Many of the principles discussed above in connection with FIGS. 4A-4D can be applied again to closure device 200. Thus, for example, one or both sets of fingers 220a/220b can support a web or sheet of blood-impervious fabric or other material to help device 200 prevent blood flow through the aperture being closed. As another example, finger sets 220 can deploy into geometric shapes (e.g., cups, arcuate portions of tube walls, etc.) that conform to the tissue surfaces to be contacted (engaged) by those fingers. These shapes may be nesting or concentric. The spacing between finger sets 220 (provided by the length of central structure 210) can be related to (e.g., slightly less than) the thickness of the tissue at the aperture to be closed to ensure that this tissue is securely (but not excessively) clamped between the two sets of fingers 220. Just as features described for device 100 can apply again to device 200, features described here for device 200 can apply again to device 100 (and all of these features can apply to later-described embodiments, and features from those later embodiments can apply to embodiments 100 and 200).

Recapitulating and in some respects extending what is said above, the spider closure mechanism 200 (FIGS. 5A and 5B) can have the following features:

1) Collapse (FIG. 5A) when in a delivery system and expand (FIG. 5B) to conform to anatomy when deployed.

2) The movable members 220 can be made from a shape-memory alloy wire, tube, or flat sheet.

3) Device 200 may also include (a) fabric (not shown) sutured or sonically welded, or (b) sutured pericardial tissue (also not shown), between movable members 220 to ensure proper sealing and tissue in-growth.

4) Fingers 220 can form two concentric cones (analogous to what is shown in FIG. 4A) to attach to the internal and external aspects of the apex of the patient's heart (assuming that the aperture to be closed is through the apex of the heart).

5) Fingers 220 can be different lengths, offset at different angles, etc., to best conform to the anatomy.

6) Device 200 can be deployed with both sides attached to a center hinge section 210, or can be ratcheted, screwed, etc., together separately. This is again analogous to a point made earlier in relation to device 100, namely, that each set of fingers 220 and an associated portion of central structure 210 can be initially separate, and these two assemblies can then be put together to form complete closure device 200.

7) Center hinge section 210 can be rigid, semi-rigid, or made of a flaccid fabric to allow closure of the hole and optimal sealing.

Figure 6:
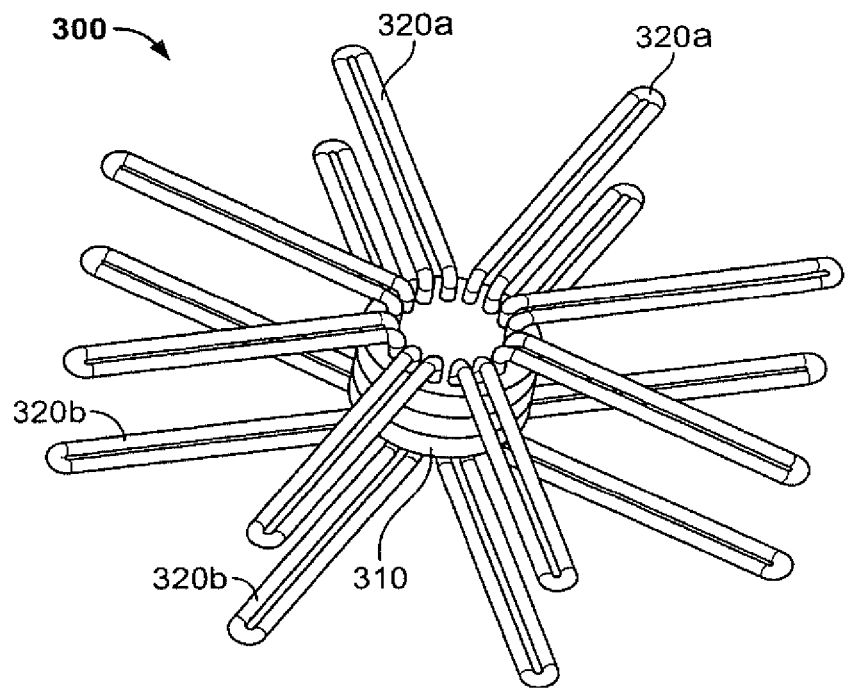
FIG. 6 is a simplified isometric or perspective view of an illustrative embodiment of other possible apparatus in accordance with the invention.

Another illustrative embodiment of a tissue access aperture closure device 300 in accordance with the invention is shown in FIG. 6. This type of structure may sometimes be referred to as a flower design. FIG. 6 shows closure device 300 in the deployed condition. Closure device 300 includes two sets of U-shaped members 320a and 320b that are resiliently biased to extend radially out from respective opposite ends of central structure 310 like the petals of a daisy-like flower. Thus, FIG. 6 shows device 300 in a condition like that shown for device 200 in FIG. 5B, and in this condition device 300 can perform in very much the same manner to close an aperture through tissue. Thus, to close such a tissue aperture, central structure 310 extends through the aperture, and members 320 engage both sides of the tissue surrounding the aperture. Structure 300 can be elastically deformed from the condition shown in FIG. 6 to a collapsed condition for delivery into the patient (e.g., through a tube-like delivery apparatus) by bending members 320a upwardly approximately parallel to one another, and by bending members 320b downwardly approximately parallel to one another (to give the thus-collapsed device 300 an appearance somewhat like what is shown in FIG. 5A for device 200). It will be appreciated that various additional features described above for devices 100 and 200 can be applied again to device 300.

Again recapitulating and in some respects extending the foregoing, the flower closure mechanism 300 (FIG. 6) can include the following features:

1) Elastically collapse when in a delivery system, and later resiliently expand (as shown in FIG. 6) to conform to anatomy when deployed.

2) The movable members 320 can be made from a shape-memory alloy wire, tube, or flat sheet.

3) Device 300 may also include (a) fabric (not shown) sutured or sonically welded, or (b) sutured pericardial tissue (also not shown), between movable members 320 to ensure proper sealing and tissue in-growth.

4) Can form two concentric or nesting cups or cones to attach to the internal and external aspects of the apex (assuming that the aperture to be closed is through the apex of the patient's heart).

5) Double (U-shaped) prongs 320 have more torsional rigidity than the single ones 220 used in the above spider design, but can still be of different lengths, offset at different angles, etc., to best conform to the anatomy.

6) Device 300 can be deployed with both sides attached to a center hinge section 310 or can be ratcheted, screwed, etc., together from two initially separate subassemblies.

7) Center hinge section 310 can be rigid, semi-rigid, or made of a flaccid fabric to allow closure of the hole and optimal sealing.

Figure 7:
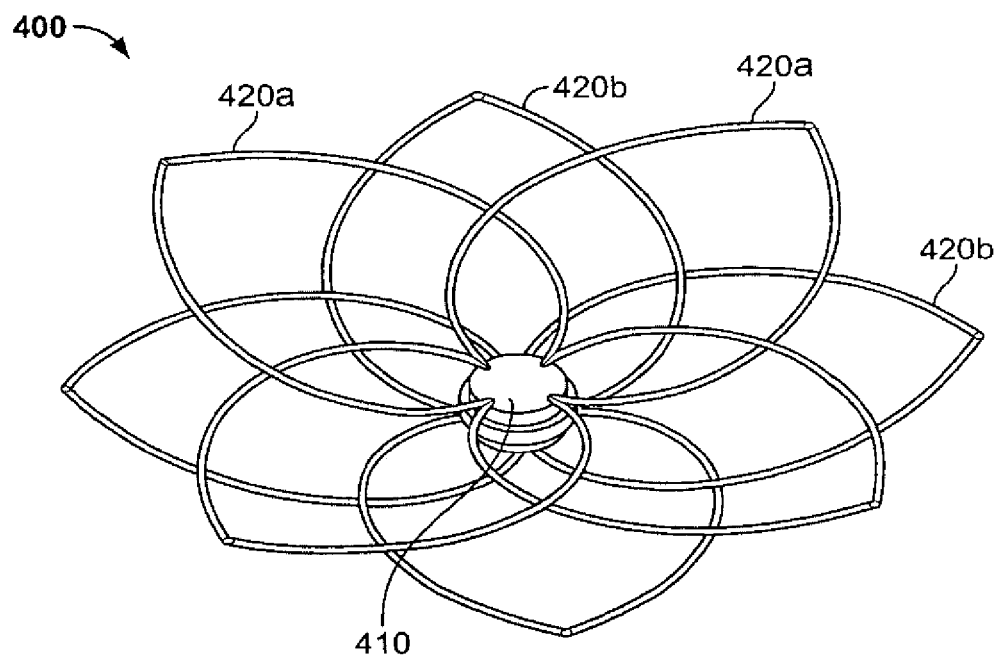
FIG. 7 is a simplified isometric or perspective view of an illustrative embodiment of still other possible apparatus in accordance with the invention.

Still another illustrative embodiment of a tissue access aperture closure device 400 in accordance with the invention is shown in FIG. 7. This type of structure may sometimes be referred to as a weave design. FIG. 7 shows device 400 in the deployed condition. Device 400 includes a central structure 410, and a web of woven, knitted, felted, or otherwise assembled wire strands extending substantially radially outwardly in all directions from each end of the central structure. To avoid over-complicating the drawings, only a few representative strands of each of these webs are shown in FIG. 7. Representative strands in the upper web have reference number 420*a*. Representative strands in the lower web have reference number 420*b*. These two webs are also sometimes referred to, respectively, by these reference numbers.

When deployed to close a tissue aperture, central structure 410 extends through the aperture, and each of webs 420*a* and 420*b* engages a respective surface of the tissue around the aperture. Each of webs 420*a* and 420*b* can be elastically collapsed to a much smaller size (e.g., to a shape something like a cylinder) for delivery into the patient (e.g., through the lumen of a tubular delivery apparatus like sheath 30 or the like). When released from confinement within such tubular delivery apparatus, webs 420 resiliently return to the conditions shown in FIG. 7. In other respects, closure device 400 can include features like those described elsewhere herein for other embodiments.

Once again recapitulating and in some respects extending the foregoing, the weave closure mechanism 400 (FIG. 7) can include the following features:

1) Elastically collapse when in a delivery system, and then resiliently expand (e.g., as shown in FIG. 7) to conform to anatomy when deployed.

2) The movable members 420 can be made from a shape-memory alloy wire, tube, or flat sheet.

3) Device 400 may also include (a) fabric (not shown) sutured or sonically welded, or (b) sutured pericardial tissue (also not shown), between movable members 420 to ensure proper sealing and tissue in-growth.

4) Can form two nesting or concentric cones or cups to attach to the internal and external aspects of the apex of the heart (again assuming that the aperture to be closed is through the apex of the heart).

5) Thin members 420*a* and 420*b* can be overlapping wires or cut as large single sections.

6) Device 400 can be deployed with both sides attached to a center hinge section 410 or can be ratcheted, screwed, etc., together from initially separate subassemblies.

7) Center hinge section 410 can be rigid, semi-rigid, or made of a flaccid fabric to allow closure of the hole and optimal sealing.

Figure 8:
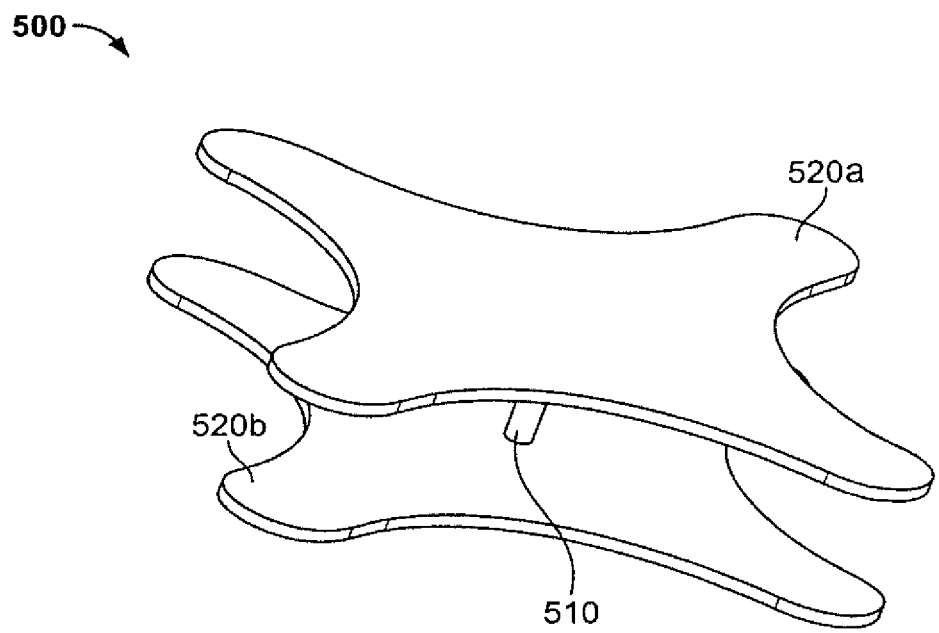
FIG. 8 is a simplified isometric or perspective view of an illustrative embodiment of other possible apparatus in accordance with the invention.

Yet another illustrative embodiment of a tissue access aperture closure device 500 in accordance with the invention is shown in FIG. 8. This type of structure may sometimes be referred to as a starfish design. Device 500 includes a central linking or connecting structure 510 (conceptually similar to elements 110, 210, 310, and 410 in earlier-described embodiments). Device 500 further includes two web or sheet-like members 520 and 520*b* at respective opposite ends of linking structure 510. Members 520*a* and 520*b* are conceptually similar to elements 120, 220, 320, and 420 in the earlier-described embodiments. Each of web members 520 is flexible but resiliently biased to take the form (shape) shown in FIG. 8. In addition, however, each of members 520 is elastically deformable to a much smaller size for delivery into the patient (e.g., through the lumen of a tube-like delivery apparatus). For example, member 520*a* may be elastically foldable upwardly as viewed in FIG. 8 into a more cylindrical shape, and member 520*b* may be elastically foldable downwardly as viewed in FIG. 8 into another more cylindrical shape. When subsequently released from tubular constraint, structure 500 resiliently returns to the shape shown in FIG. 8. Because device 500 is so conceptually similar to other, previously described embodiments, this description of device 500 will be sufficient for those skilled in the art. It is expressly noted, however, that features and aspects described elsewhere herein for other embodiments can be applied as appropriate, to the FIG. 8 embodiment.

Again recapitulating and in some aspects extending the foregoing, the starfish closure mechanism 500 (FIG. 8) can include the following features:

1) Elastically collapse when in a delivery system and then resiliently expand (e.g., as shown in FIG. 8) to conform to anatomy when deployed.

2) The movable members 520 can be made from a shape-memory alloy wire, tube, or flat sheet.

3) Members 520 may also include (a) fabric sutured or sonically welded, or (b) sutured pericardial tissue, on a movable substructure to ensure proper sealing and tissue in-growth. Such a substructure can itself be a web or sheet-like structure, or it can be a more open frame-like structure (e.g., a grid of intersecting wire-like members or the like).

Figure 9:
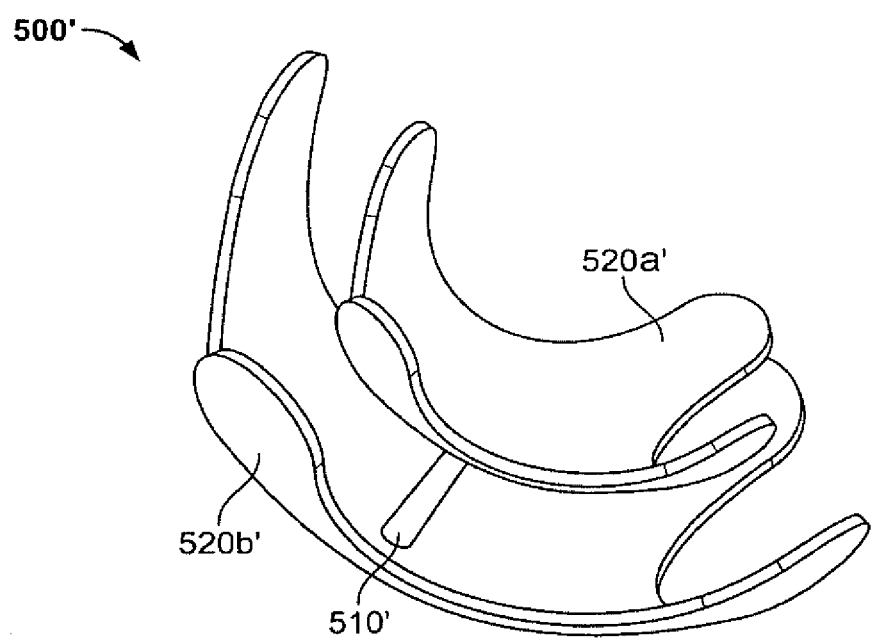
FIG. 9 is a simplified isometric or perspective view of an illustrative embodiment of still other possible apparatus in accordance with the invention.

4) Members 520*a* and 520*b* can form two nesting or concentric cones or cups to attach to the internal and external aspects of the apex of the heart (e.g., as in FIG. 9; for closing access through the side wall of a tubular vessel such as the aorta, other deployed shapes such as in FIG. 10 may be employed)

5) Winged sealing sections 520 can be outlined, woven, etc., in any suitable manner to provide any desired degree of stiffness or flexibility.

6) Device 500 can be deployed with both sides attached to a center hinge section 510 or can be ratcheted, screwed, etc., together from initially separate components or subassemblies.

7) Center hinge section 510 can be rigid, semi-rigid, or made of a flaccid fabric to allow closure of the hole and optimal sealing.

FIG. 9 is provided to further illustrate the point that a closure device like 500 (now numbered 500') can be constructed so that web-like members 520*a'* and 520*b'* are resiliently biased to form nesting cone or cup shapes (suitable, for example, for closing an aperture in the apex of the heart). This possibility was already mentioned earlier, and once again it is pointed out that this principle can be applied to any of the closure device embodiments shown herein. Similarly, FIG. 10 is provided to further illustrate the point that a closure device like 500 (now numbered 500") can be constructed so that web-like members 520" and 520*b"* are resiliently biased to form arcuate portions of the surfaces of concentric tubes (suitable, for example, for closing an aperture in the side wall of a tubular blood vessel such as the aorta or the vena cava). This possibility was also mentioned earlier, and again it is pointed out that this principle can be applied to any of the closure device embodiments shown herein.

Note that in all embodiments of the closure devices (e.g., 100, 200, 300, etc.) in accordance with the invention, deployment of the device typically proceeds in successive stages. For example, the (tubular) delivery device for the closure device typically initially extends through the tissue aperture to be closed. The closure device is then pushed distally part way out of the distal end of the delivery device so that the part of the closure device that will remain inside the circulatory system (e.g., 120a, 220a, 320a, etc.) can deploy (expand) inside that system. The delivery device is then proximally retracted from the tissue aperture, while the remainder of the closure device is pushed or pulled out of the distal end of the delivery device. This ultimately allows the part of the closure device that will be left outside of the circulatory system (e.g., 120b, 220b, 320b, etc.) to deploy outside of the circulatory system. The linking structure (e.g., 110, 210, 310, etc.) between the inner and outer parts of the closure device remains in the tissue aperture between the deployed (expanded) inner and outer parts of the closure device.

Figure 11:
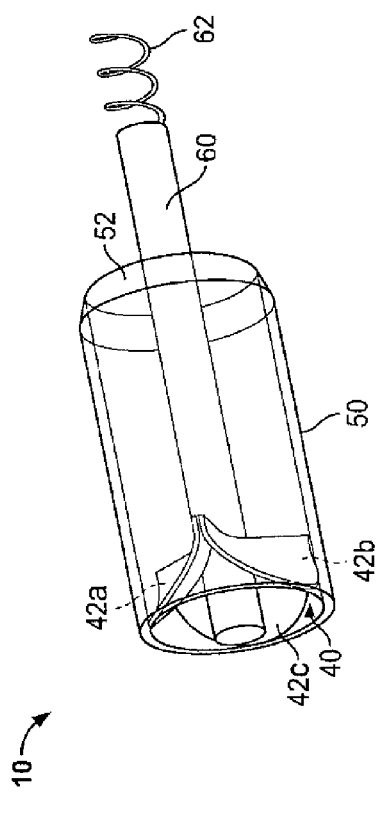
FIG. 11 is a simplified isometric or perspective view of an illustrative embodiment of possible apparatus in accordance with the invention.
Figure 12:
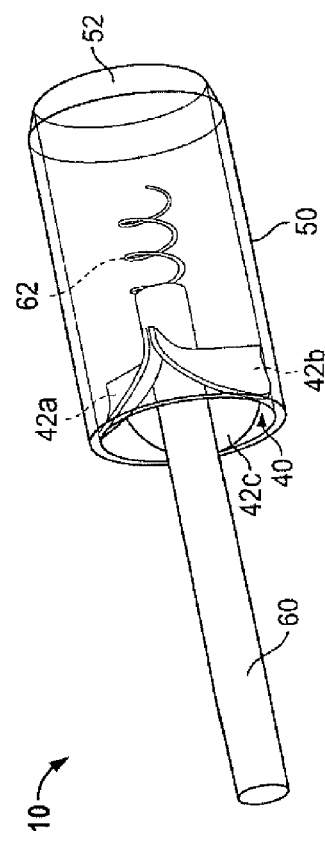
FIG. 12 is similar to FIG. 11 for a different operating condition of the FIG. 11 apparatus.
Figure 13:
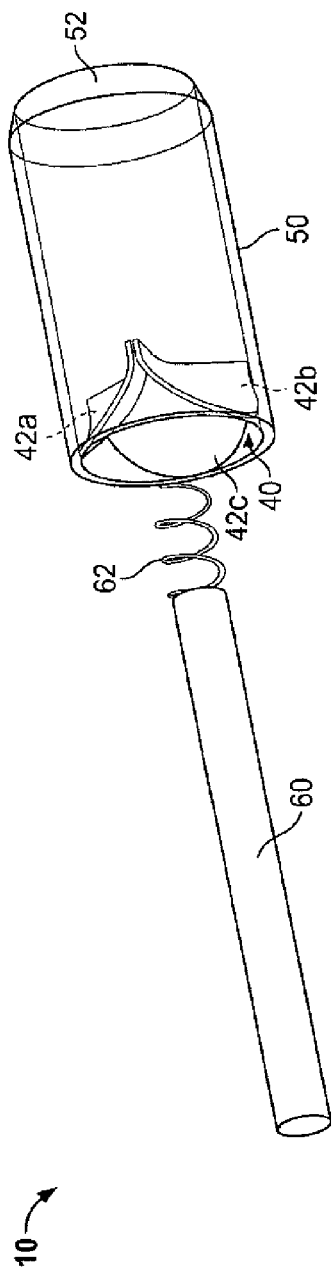
FIG. 13 is again similar to FIG. 11 for another different operating condition of the FIG. 11 apparatus.

FIG. 11-13 show an illustrative embodiment of how a one-way valve 40 (like the valve 40 in FIG. 1) may be included within a coring or cutting device 10 (like the coring device 10 in FIGS. 2A and 2B). The bases of the three flexible leaflets 42a-c of valve 40 are sealingly secured to the inner surface of the tube 50 of cutter 10. FIG. 11 shows the corkscrew 62 with its rod 60 passing through the center of valve 40 and in a position to engage and hold onto tissue. Backflow of blood (from right to left as viewed in FIG. 11) is stopped by valve 40, the three flexible and resilient leaflets 42a-c of which are closed around rod 60.

Moving on to FIG. 12, once the tissue (not shown) is secured by corkscrew 62 and the cutter 50 (especially the sharpened, circular, distal edge 52 of the cutter) cores a circular section of the tissue, corkscrew 62, rod 60, and the tissue core (on corkscrew 62) are retracted. FIG. 13 shows further retraction of corkscrew 62, rod 60, and the tissue core (still not shown, but still on corkscrew 62) through valve 40. Valve 40 now fully closes on itself and thus continues to prevent blood flow (from right to left) through cutter 10.

Figure 14:
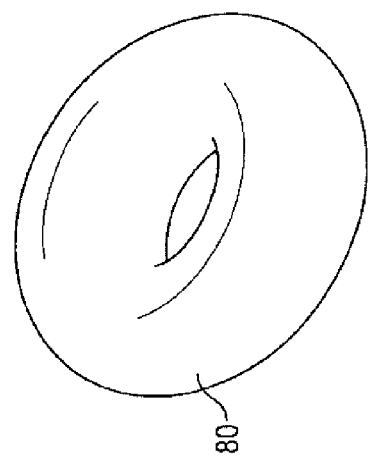
FIG. 14 is a simplified isometric or perspective view of an illustrative embodiment of other possible apparatus in accordance with the invention.
Figure 15:
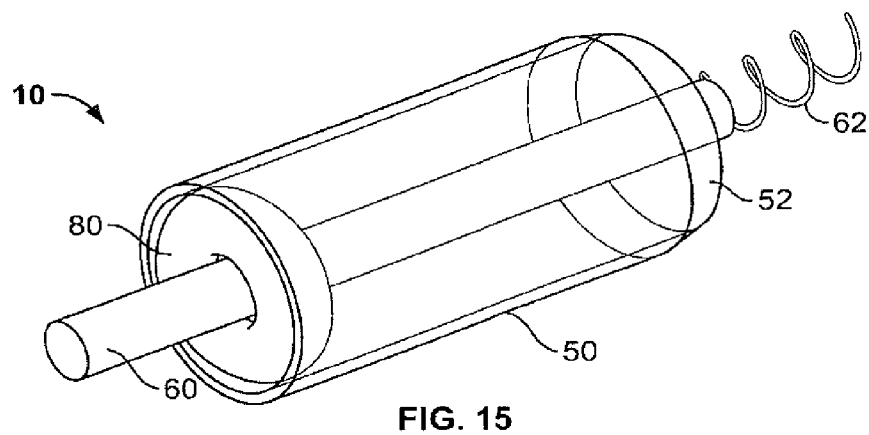
FIG. 15 is a simplified isometric or perspective view of an illustrative embodiment of still more possible apparatus in accordance with the invention.

FIGS. 14 and 15 show that instead of using a valve with multiple flexible and resilient leaflets (as in FIGS. 1 and 11-13), a semi-solid or balloon-expanded toroid 80 can be used (as a valve) to stop blood flow. FIG. 14 shows toroid 80 by itself, while FIG. 15 shows toroid 80 mounted inside the tube 50 of cutter 10. In particular, a radially outermost circular periphery of toroid 80 is sealingly secured to the inner surface of tube 50. FIG. 14 shows how the corkscrew rod 60 can pass through the center of toroid 80 without allowing the backflow of blood (from right to left as viewed in FIG. 15).

Figure 16:
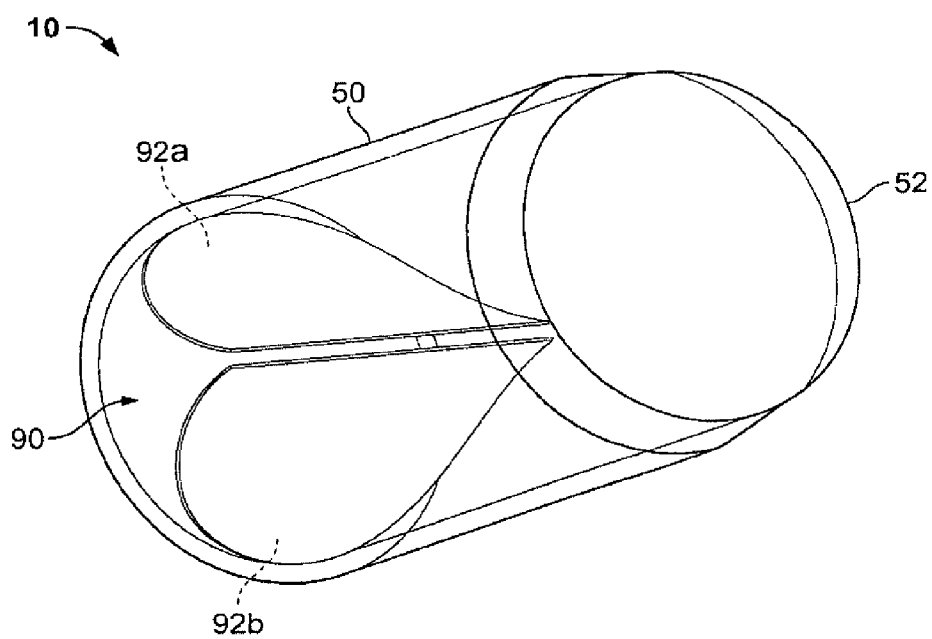
FIG. 16 is a simplified isometric or perspective view of another illustrative embodiment of possible apparatus in accordance with the invention.

Still other valve configurations for blocking blood flow are possible. For example, FIG. 16 shows a bi-leaflet valve 90 inside the tube 50 of cutter Leaflet 90 has two flexible and resilient leaflets 92a and 92b. The material of these leaflets can be similar to the material of leaflets 42 in earlier-described valve 40, or the material of these leaflets (92) can be different. For example, it may be desirable to use a more elastic (stretchable) material for leaflets 92. The U-shaped edge of each leaflet 92 is sealingly secured to the inner surface of tube 50. The straight, relatively free edges of the leaflets come together along a diameter that extends across the inside of tube 50. When these free edges are thus together, valve 90 is "closed" and prevents blood flow from right to left through tube 50. However, leaflets 92 allow other instrumentation (like elements 60 and 62) to pass between them, while still maintaining a seal around that other instrumentation to prevent blood flow from right to left through tube 50.

Finally, it is again pointed out that although the apex of the heart (e.g., the apex of the left ventricle) is frequently mentioned above for access, the invention is also applicable to access from the right ventricle (which may be thinner than the left ventricle near the apex), through a major vessel such as the aorta or vena cava, or in other ways mentioned earlier in this specification. Also, the valve may be delivered from the blood outflow side (e.g., from the aorta (in the example of aortic valve replacement through the side wall of the aorta)) or from the blood inflow side (e.g., from the apex (in the example of aortic valve replacement through the apex)). Any of the closure device designs shown herein can be contoured to fit a tubular vessel (FIG. 10 is an example of a suitable contour), or can be cup- or cone-shaped to fit the apex (FIG. 9 is an example). In addition to aortic valve replacement, the invention is also applicable to LV access for mitral valve replacement, RV access for pulmonic valve replacement, and the like.

The invention claimed is:

1. An apparatus for closing an aperture through a wall of a structure within a patient's circulatory system, comprising:
a solid central structure having an outer perimeter and a longitudinal axis;
a first portion operatively coupled to the central structure within the outer perimeter and transitionable between a collapsed condition and an expanded condition, the first portion being formed from a first web of interwoven wire strands, the first web extending radially outward from the longitudinal axis by a greater amount in the expanded condition than in the collapsed condition, and being configured to conform to an inner surface of tissue around the aperture when in the expanded condition; and
a second portion operatively coupled to the central structure within the outer perimeter and transitionable between a collapsed condition and an expanded condition, the second portion being formed from a second web of interwoven wire strands, the second web extending radially outward from the longitudinal axis by a greater amount in the expanded condition than in the collapsed condition, and being configured to conform to an outer surface of tissue around the aperture when in the expanded condition,
wherein the first portion is operatively coupled to the second portion within the outer perimeter of the central structure and the apparatus has a longer length when the first portion and the second portion are in the collapsed condition than when the first portion and the second portion are in the expanded condition.

2. The apparatus of claim 1, wherein the first portion and the second portion are resiliently biased toward the expanded condition.

3. The apparatus of claim 1, wherein the central structure is configured to substantially fill the aperture.

4. The apparatus of claim 1, wherein the central structure is configured to hold the first portion against the inner surface of tissue around the aperture and to hold the second portion against the outer surface of tissue around the aperture.

5. The apparatus of claim 1, wherein the first portion has a convex shape in the expanded condition as viewed from the second portion.

6. The apparatus of claim 1, wherein the second portion has a concave shape in the expanded condition as viewed from the first portion.

7. The apparatus of claim 1, wherein the first portion has a cup-like shape in the expanded condition.

8. The apparatus of claim 1, wherein the first portion has an arcuate shape in the expanded condition.

9. The apparatus of claim 1, wherein the first portion has the shape of an arcuate surface of a cylinder in the expanded condition.

10. The apparatus of claim 1, wherein the first portion includes a plurality of members projecting radially outward from the longitudinal axis in the expanded condition.

11. The apparatus of claim 1, further comprising a web of material assembled between the first portion and the second portion.

12. The apparatus of claim 11, wherein the web of material comprises a fabric.

13. The apparatus of claim 11, wherein the web of material comprises biological tissue.

* * * * *